United States Patent [19]

Shansky et al.

[11] Patent Number: 4,767,617
[45] Date of Patent: Aug. 30, 1988

[54] OPACIFYING COMPOSITION AND HAIR TREATING COMPOSITION WITH PROCESS OF USING SAME

[75] Inventors: Albert Shansky, Norwalk, Conn.; Prakash C. Purohit, Minneapolis, Minn.

[73] Assignee: A-Veda Corporation, Minneapolis, Minn.

[21] Appl. No.: 892,130

[22] Filed: Jul. 31, 1986

[51] Int. Cl.$^4$ ........................... A61K 7/09; A45D 7/00
[52] U.S. Cl. .......................................... 424/71; 424/72; 132/7
[58] Field of Search ......................... 424/71, 72; 132/7

[56] References Cited

U.S. PATENT DOCUMENTS

| | | | |
|---|---|---|---|
| 3,171,786 | 3/1965 | Shansky | 424/DIG. 2 |
| 3,912,808 | 10/1975 | Sokol | 424/71 |
| 3,950,510 | 4/1976 | Adams | 424/71 |
| 4,260,550 | 4/1981 | Armstrong et al. | 424/70 |
| 4,265,782 | 5/1981 | Armstrong et al. | 424/70 |
| 4,364,837 | 12/1982 | Pader | 424/70 |
| 4,507,278 | 3/1985 | DeMarco et al. | 424/70 |

Primary Examiner—Albert T. Meyers
Assistant Examiner—F. L. Krosnick
Attorney, Agent, or Firm—Peterson, Wicks, Nemer & Kamrath

[57] ABSTRACT

An opacifier composition for use in permanent waving compositions and neutralizer compositions associated therewith. The opacifier composition is an aqueous emulsion containing: (a) methyl ester of hydrogenated rosin acids, (b) an alkylene glycol such as octylene glycol, and (c) a mixture of nonionic surfactants, such as the polyoxyethylene ethers of fatty alcohols, for example lauryl alcohol. The use of the opacifier composition eliminates or minimizes hair breakage which occurs with other opacifier systems such as those employing latex emulsions.

2 Claims, No Drawings

OPACIFYING COMPOSITION AND HAIR TREATING COMPOSITION WITH PROCESS OF USING SAME

BACKGROUND OF THE INVENTION

1. Field of the Invention

This invention relates to opacifying compositions adapted for use in hair treating compositions, such as hair setting or waving formulations, including the neutralizer formulations applied after the waving solution.

2. Description of Prior Art

Cold waving or permanent waving of the hair has been known for some time. In salons, heat is sometimes applied. In so-called home "perms" generally no heat is applied. The usual procedure involves, in its simplest terms, the application of a hair waving solution or lotion to the hair which softens the hair and allows for reshaping of the hair. Subsequently, the hair is set into the new shape by application of a neutralizing agent.

Traditionally, permanent wave lotions and neutralizers have been made opaque by using synthetic whitening agents. Opacity is aesthetically desired as it conveys an impression of softness or mildness. The usual opacifying materials now employed are latex emulsions (generally based on styrene/acrylates polymers). Others can be seen from (a) U.S. Pat. No. 3,171,786 which employs a fatty amide in a solvent, such as a nonylphenoxypoly(ethyleneoxy)ethanol which when employed with a polyvinyl pyrrolidone hair setting formulation provides the desired opacity, and (b) U.S. Pat. No. 4,460,488 which employs certain plant residues as an opacifying agent.

Typical latex emulsions employed, which are styrene-acrylate or acrylamide polymers, are opacifiers supplied by Morton Chemical Company under designations E-284, 288, 295, 300, 305 and 308. Such latex emulsions, as used, are employed in permanent wave lotions or neutralizers in amounts of 1-2% concentration by weight. The latex emulsions, while useful as opacifying agents, have serious drawbacks in that they are somewhat substantive to the hair and as such can cause the hair to snag during combing, thereby causing the hair to break.

SUMMARY OF THE INVENTION

It has now been found that certain derivatives of rosin acids (abietic acids) can be formulated to provide a particularly desirable opacifier or opacifying composition particularly useful in permanent waving solutions and neutralizing solutions employed therewith.

Accordingly, the present invention provides an opacifying composition particularly adapted for use in hair treating compositions, such as permanent waving lotions and neutralizing solutions. This opacifying composition makes use of an alkyl ester of hydrogenated rosin acids in combination with an alkylene glycol and a mixture of nonionic surfactants which provide a suitable hydrophilic-lipophilic balance.

The opacifying composition may generally be described as comprised of an aqueous solution of (a) An alkyl ester of hydrogenated rosin acids wherein the alkyl group contains about 1-4 carbon atoms, preferably the methyl group;

(b) An alkylene glycol wherein the alkylene group contains about 6-10 carbon atoms and preferably is a branched chain alkylene group of 8 carbon atoms; and (c) A mixture of nonionic polyoxyalkylene surfactant having a certain hydrophilic-lipophilic balance, the preferred mixture being an equal weight mixture of two polyoxyethylene ethers of certain fatty alcohols wherein (1) one has an HLB of about 10 and (2) the other has an HLB of about 17.

By weight the composition will be composed of about 8–30% of (a); about 0.8–3.0% of (b) and about 1.5–6% of (c)(1) and (c)(2) above, preferably in substantially equal proportions by weight.

The opacifying composition will be added to permanent wave or neutralizer compositions in amounts of about 0.5–3%, and preferably on the order of 1–2% by weight.

DETAILED DESCRIPTION OF THE PREFERRED EMBODIMENTS

As is apparent from the Summary of the Invention, the opacifying composition is an aqueous solution for dispersion of (a) the alkyl ester of hydrogenated rosin acids; (b) a glycol, and (c) a mixture of certain nonionic polyoxyalkylene surfactants to provide a desirable hydrophilic-lipophilic balance.

The alkyl esters of hydrogenated rosin acids are the lower alkyl esters containing about 1–4 carbon atoms. The esters are described as esters of rosin acids as they are derived from rosin. It is not intended that these be resinous in character but only that the acids are derived from rosin. The acids derived from rosins are $C_{20}$ fused ring monocarboxylic acids such as levopimaric and abietic acids. The acids may be hydrogenated to reduce unsaturation by the addition of hydrogen under pressure. The lower alkyl esters of the acids are prepared by an esterification of the rosin acids with simple lower alkynols containing 1–4 carbon atoms, such as methanol. The methyl esters of hydrogenated rosin acids are available commercially from Hercules Corporation as Hercolyn D. This is the preferred material for use in the present invention.

Component (b) of the opacifier composition is an alkylene glycol in which the alkylene group contains from 6–10 carbon atoms. Octylene glycols are preferred, particularly those in which the alkylene group is branched, such as in 2-ethyl-1,3-hexane diol.

Components (c) of the opacifier composition are a mixture of nonionic polyoxyalkylene surfactants, one having a hydrophilic-lipophilic balance (HLB) number of about 10 and the other having an HLB of about 17. This mixture provides a desirable hydrophilic-lipophilic balance of about 13 to 14 when employed in an equal weight mixture with the Hercolyn D and the 2-ethyl-1,3-hexane diol.

With other esters and glycols the amounts of compounds (c)(1) and (c)(2) may be varied to provide optimum properties but will generally lie in the relative proportions or ratio of (c)(1) to (c)(2) of about 2:1 to about 1:2. The amounts are adjusted to provide an appropriate hydrophilic-lipopilic balance to form an emulsion containing the rosinate ester.

The nonionic surfactants for use in this invention are generally described as polyoxyalkylene ethers of fatty alcohols wherein the alkylene group contains from 2–4 carbon atoms and the fatty alcohol has from 10–20 carbon atoms. The preferred surfactants are the polyoxyalkylene ethers, such as the polyoxyethylene ether, of fatty alcohols containing about 12–18 carbon atoms, such as lauryl alcohol, cetyl alcohol, oleyl and stearyl alcohols. To exemplify the present invention, polyoxyethylene ethers of lauryl alcohol available from ICI Americas, Inc. as Brij 30 and Brij 35 were employed. Brij 30 is the polyoxyethylene ether of lauryl alcohol containing four ethyleneoxy groups and has an HLB of about 10. Brij 35 is the polyoxyethylene ether of lauryl alcohol containing 23 ethyleneoxy units and has an HLB of about 17. These may generally be defined by means of the idealized formula:

$$CH_3(CH_2)_{10}CH_2(OCH_2CH_2)_nOH$$

wherein n is an integer indicating the number of repeated ethyleneoxy units, 4 in the case of Brij 30 and 23 in the case of Brij 35. The integer n will generally lie in the range of 2-25 and compound (c) is a mixture of one surfactant having a lower number of repeating oxy alkylene units (2-8) while the other has a larger number of repeating oxy alkylene units (10-25).

The opacifier composition is accordingly an aqueous solution of (a) 8-30% of the ester of hydrogenated rosin acids preferably the methyl ester; (b) 0.8-3.0% of the branched chain alkylene glycol; and (c) an equal weight mixture (1.5-6% each) of nonionic surfactants which are polyoxyalkylene ethers of fatty alcohols, one having an HLB number of about 10 and the other having an HLB number of about 17.

At the above usage levels, component (a) of the opacifying agent will be present in the final permanent wave composition, or neutralizer composition, in an amount of about 0.04-0.24%, and preferably about 0.08-0.16%. Correspondingly component (b) and (c)(1) (c)(2) would accordingly be present in the final wave composition or neutralizer in an amount of respectively about 0.004-0.024%, preferably about 0.008-0.016% and about 0.0075-0.045%, preferably about 0.015-0.3% of (c)(1) and (c)(2) respectively.

The remainder of the opacifier, which is sometimes referred to as a cold wave cloud composition, is water. This aqueous solution provides the correct or desired turbidity in permanent wave or neutralizer compositions when employed in an amount of about 1% by weight. The opacifier cloud composition will generally be employed in an amount of 0.5-3% by weight, more desirably 1-2% with about 1% being preferred. There are thus provided improved permanent waving and neutralizing compositions containing the usual hair treating chemicals and the opacifier, wherein the improved waving or neutralizing solution contains from 0.5-3% by weight of the opacifier composition in the present invention. In addition to the hair treating chemicals the compositions will contain the usual fragrances, essential oils, surfactants and the like.

The following examples will serve to illustrate the present invention in which all parts and percentages are by weight unless otherwise specified.

EXAMPLE 1

In this example, an emulsion is prepared by heating two phases separately to 50° C. The first phase is water only. The second phase (oil phase) contains the methyl ester of the hydrogenated rosinate (Hercolyn D) plus the other ingredients. The emulsion is prepared by adding the oil phase to the water phase and maintaining the temperature at 50° C. while vigorously mixing.

The composition of the preferred opacifier composition on a percentage of weight basis is as follows:

| Ingredient | Amount (in grams) | % by weight |
|---|---|---|
| Water | 225 | 75.00 |
| Hercolyn D* | 50 | 16.67 |
| Octylene Glycol** | 5 | 1.67 |
| Brij 35*** | 10 | 3.33 |
| Brij 30**** | 10 | 3.33 |

*Methyl hydrogenated rosinate - Hercules Inc., Wilmington, DE.
**2-Ethyl-1, 3-hexane diol - Union Carbide Corp., Danbury, CT.
***Polyethylene glycol ether of lauryl alcohol with 4 moles of ethylene oxide--ICI Americas, Inc., Wilmington, DE.
****Polyethylene glycol ether of lauryl alcohol with 23 moles of ethylene oxide - ICI Americas, Inc., Wilmington, DE.

EXAMPLE 2

In this example two permanent wave lotions are prepared containing the opacifier composition of Example 1, having the formulations set out below:

| Ingredient | % by weight |
|---|---|
| Perm Lotion A | |
| Water | 77.90 |
| Monoethanolamine thioglycolate (40%) | 18.00 |
| Monoethanolamine (99%) | 2.50 |
| Polyoxysorbitan mono laurate* | 0.50 |
| Melissa essential oil | 0.10 |
| Hercolyn opacifier | 1.00 |
| pH = 9.3 | |
| % Thioglycolate = 7.3 | |
| Perm Lotion B | |
| Water | 81.80 |
| Ammonium thioglycolate (60%) | 12.00 |
| Ammonium hydroxide (28%) | 3.30 |
| Sodium hydroxide (50%) | 1.30 |
| Polyoxysorbitan mono laurate* | 0.50 |
| Melissa essential oil | 0.10 |
| Hercolyn opacifier | 1.00 |
| pH = 9.3 | |
| % Thioglycolate = 7.3 | |

*Tween 20 - supplied by ICI Americas, Inc.

EXAMPLE 3

In this example two neutralizer lotions are prepared containing the opacifier composition of Example 1, and having the formulations set out below.

| Ingredient | % by weight |
|---|---|
| Neutralizer A | |
| Water | 87.885 |
| Glycerin | 3.000 |
| Hydrogen peroxide (35%) | 7.500 |
| Phosphoric acid (8.5%) | 0.015 |
| Polyoxysorbitan mono laurate* | 0.500 |
| Ylang-ylang essential oil | 0.100 |
| Hercolyn opacifier | 1.000 |
| pH = 3.79 | |
| % Hydrogen Peroxide = 2.50 | |
| Neutralizer B | |
| Water | 83.40 |
| Glycerin | 3.00 |
| Sodium bromate | 12.00 |
| Polyoxysorbitan mono laurate* | 0.50 |
| Ylang-ylang essential oil | 0.10 |
| Hercolyn opacifier | 1.00 |
| pH = 6.5 | |
| % Bromate = 12.00 | |

*Tween 20 - supplied by ICI Americas, Inc.

Using the opacifier composition of Example 1 in a permanent waving lotion as set out in Example 2, and using a neutralizer as set out in Example 3, serve to show that the opacifier composition can be employed as a direct replacement for the usual latex emulsions without suffering the drawbacks, such as hair breakage, associated with latex emulsions.

What is claimed:

1. In a hair treating composition selected from the group consisting of permanent wave and permanent wave neutralizer compositions containing an effective opacifying amount of an opacifier, the improvement wherein said opacifier is an opacifier composition on a weight basis consisting of:
   (a) from 8-30% of a methyl ester of hydrogenated rosin acids,
   (b) from 0.8-3.0% of 2-ethyl-1,3-hexane diol,
   (c) a mixture of nonionic surfactants of:
       (1) 1.5-6% of a polyoxyethylene ether of lauryl alcohol having an HLB of about 10 and,
       (2) 1.5-6% of a polyoxyethylene ether of lauryl alcohol having an HLB of about 17 so as to provide a hydrophilic-lipophilic balance of about 13-14, and,
   (d) the remainder being water.

2. In a process for the permanent shaping of human hair which comprises:
   (a) applying to the hair a permanent waving composition and thereafter
   (b) applying a permanent wave neutralizing composition to set the shape of said hair, the improvement wherein each of said permanent waving composition and said permanent wave neutralizing composition contains an effective opacifying amount of an opacifier and said opacifier is an opacifier composition of a weight basis consisting of an aqueous emulsion of:
   (1) about 8-30% of a methyl ester of hydrogenated rosin acids,
   (2) about 0.8-3.0% of a branched alkylene glycol wherein the alkylene group contains about 6-10 carbon atoms, and
   (3) a mixture of about 1.5-6% of each of two nonionic surfactants comprised of polyoxyalkylene ethers of a fatty alcohol and wherein said alkylene group of said polyoxyalkylene ethers contains 2-4 carbon atoms and said fatty alcohol contains 10-20 carbon atoms, said nonionic surfactants being in an equal ratio by weight and one of said nonionic surfactants having an HLB of about 10 and the second of said nonionic surfactants having an HLB of about 17 so as to provide a hydrophilic-lipophilic balance of about 13-14.

* * * * *